United States Patent [19]
Herwig et al.

[11] Patent Number: 6,025,524
[45] Date of Patent: Feb. 15, 2000

[54] SINGLE-STAGE PROCESS FOR THE PREPARATION OF AMINES

[75] Inventors: Jürgen Herwig, Kriftel; Richard Walter Fischer, Bad Soden; Heinz Alexander, Frankfurt; Burkhard Zimmermann, Eching; Matthias Beller, Ismaning, all of Germany

[73] Assignee: Hoechst Research & Technology Deutschland GmbH & Co. KG, Frankfurt, Germany

[21] Appl. No.: 09/138,718

[22] Filed: Aug. 24, 1998

[30] Foreign Application Priority Data

Aug. 26, 1997 [DE] Germany .............. 197 37 053

[51] Int. Cl.[7] .................................................. C07C 209/00
[52] U.S. Cl. ................................................................ 564/467
[58] Field of Search .............................................. 564/467

[56] References Cited

U.S. PATENT DOCUMENTS

| | | | |
|---|---|---|---|
| 4,292,242 | 9/1981 | Laine | 260/326.8 |
| 4,317,932 | 3/1982 | Jachimowicz | 564/445 |
| 4,794,199 | 12/1988 | Lin et al. | |

OTHER PUBLICATIONS

Catalysis Today, vol. 36, 1997, pp. 305–310.

*Primary Examiner*—Samuel Barts
*Attorney, Agent, or Firm*—Frommer Lawerence & Haug LLP

[57] ABSTRACT

The invention relates to a process for the preparation of an amine by single-stage reaction of a $C_2$–$C_{20}$-olefin with a compound having an $NH_3$ group, hydrogen and carbon monoxide, wherein the reaction takes place in the presence of a catalyst, which is present in water in dissolved or suspended form, and the catalyst contains at least two metals from group VIII of the Periodic Table of the Elements in elemental or bonded form.

46 Claims, No Drawings

SINGLE-STAGE PROCESS FOR THE PREPARATION OF AMINES

The present invention relates to a single-stage process for the preparation of amines by catalytic reaction of olefins with carbon monoxide, hydrogen and a compound having an $NH_3$ group under pressure and elevated temperature.

Amines and derivates thereof are of industrial importance as precursors for dyes, fine chemicals, pharmaceuticals, agrochemicals and as additives for lubricating oils and diesel fuels. Primary amines are usually prepared by reductive amination of aldehydes, by aminolysis of alcohols or by hydrogenation of nitriles.

The aminomethylation, i.e. the direct reaction of olefins with ammonia and synthesis gas, leads with only small yields and very poor selectivities to primary or secondary amines since these intermediates very quickly react further to give tertiary amines, and secondary reactions, such as aldol condensations of the intermediate aldehydes, arise. The literature gives only a very few examples which describe aminomethylation for the preparation of primary amines.

U.S. Pat. No. 4,794,199 describes an aminomethylation using a phosphine-modified catalyst system which contains only cobalt as catalyst metal. The reaction temperatures are, at 200° C., very high. The selectivity to primary amines is stated as 57% although only about half of these are amines which originate from direct aminomethylation. The other half of the primary amines result from the aminomethylation of the aldol condensation product. The actual selectivity to the desired low molecular weight primary amine is at most 32% in the examples described. The achieved selectivities are insufficient for industrial use.

Catalysis Today 36 (1997) p. 305–310 summarizes and explains the results of U.S. Pat. No. 4,794,199. The author concludes that more effective methods for single-stage amine preparation from olefins, synthesis gas and ammonia must be found.

The object of the present invention is to provide a single-stage process by means of which olefins, synthesis gas and ammonia can be reacted to amines with high selectivity. In addition, it is desirable that the catalyst can be readily separated off from the product.

This object is achieved according to the invention by a process for the preparation of an amine by single-stage reaction of a $C_2$–$C_{20}$ olefin with a compound having an $NH_3$ group, hydrogen and carbon monoxide, wherein the reaction takes place in the presence of a catalyst, which is present in water in dissolved or suspended form, and the catalyst contains at least two metals from group VIII of the Periodic Table of the Elements (Fe, Co, Ni, Ru, Rh, Pd, Os, Ir, Pt) in elemental or bonded form.

This process is particularly suitable for the preparation of primary or secondary amines, the choice of starting products determining whether primary or secondary amines are produced in preference. The mixture of primary and secondary amines which is produced in other cases can be separated into the individual products by processes known per se using a distillative or chromatographic method.

The novel process is particularly notable for the fact that primary or secondary amines can each be prepared with high selectivities at high conversions in a single-stage process. Tertiary amines are produced in negligible amounts.

In accordance with an advantageous embodiment, at least one of the metals from group VIII of the Periodic Table of the Elements is rhodium or iridium. The catalyst particularly preferably comprises both rhodium and iridium in elemental or bonded form, the molar ratio of rhodium to iridium being 2:1 and 1:200, in particular between 1:1 and 1:100. Particularly suitable compounds are those which contain rhodium and iridium and are water-soluble under the reaction conditions (for example water-soluble complexes); the metals of group VIII of the Periodic Table of the Elements can likewise be used in finely divided (colloidal) elemental form.

Examples of metal compounds which can be used according to the inveniton are rhodium(III) carboxylates, rhodium(III) acetylacetonate, rhodium(III) sulfate, rhodium(III) nitrate, iridium(III) acetylacetonate, iridium(III) carboxylates, iridium(III) sulfate, iridium(III) nitrate and chloro-(1,5-cyclooctadien)iridium(I) dimer.

The compound having an $NH_3$ group can be ammonia or an ammonium compound. The ammonia can be added to the reaction as gas or in the form of an aqueous solution. The aqueous solution preferably comprises from 5 to 35% by weight of ammonia at room temperature and atmospheric pressure.

The ammonium compound is preferably a compound which is readily soluble in water, it is chosen in particular from the group consisting of ammonium acetate, ammonium carbonate, ammonium chloride and ammonium bromide.

If ammonia is used as gas, its concentration is from 0.1 to 80% by weight, preferably from 5 to 80% by weight, in particular from 10 to 70% by weight, based on the aqueous phase.

If the ammonium compound is used as aqueous solution, its concentration is preferably between 1 and 80%, particularly preferably between 10 and 80 Gew. % by weight, in particular between 20 and 40% by weight, based on the aqueous phase. The amount of the compound having an $NH_3$ group is generally, per mole of olefin, between 0.1 and 100 mol, preferably between 3 and 100 mol. For a high selectivity in terms of the primary amines, it is preferably between 5 and 20 mol, whereas for a high selectivity as regards the secondary amines it is preferably between 0.3 and 0.8 mol.

The olefin can be present under the reaction conditions in a liquid water-immiscible phase.

In view of the large-scale application of this process, olefins having from 3 to 12 carbon atoms, in particular from 6 to 10 carbon atoms, are reacted preferentially. In this connection, the olefin can have up to 3 non-conjugated double bonds. Equally, the olefin used can be a cycloolefin having up to 3 carbocycles and arylvinyl compounds. It is, however, also possible to use mixtures of the aforedescribed olefins.

In particular, this process is particularly suitable for the reaction of olefins having one terminal or two non-conjugated double bonds. Compounds having a terminal double bond are preferably alkenes, alkyl alkenoates, alkylene alkanoates, alkenyl alkyl ethers and alkenols. Examples of such compounds are ethene, propene, 1-butene, 1-pentene, 1-hexene, 1-heptene, 1-octene, 1-decene, 1-nonene, 1-dodecene, 1-hexadecene, 2-ethyl-1-hexene, styrene, 3-phenyl-1-propene, 1,4-hexadiene, 1,7-octadiene, allyl propionate, 4-vinylcyclohexene, vinylnorbornene, dicyclopentadiene, tripropylene, dimersol, cyclohexene, cyclopentene, pinene and limonene.

The olefin is preferably chosen from the group consisting of propene, butene, isobutene, heptene, hexene and dicyclopentadiene.

According to a particularly preferrred process in accordance with the present invention the catalyst and the olefin are present in two different liquid phases which are immiscible with one another. Moreover, the starting materials used in the form of gases can be present under the reaction conditions in a further gaseous phase. The catalyst is in the aqueous phase, while the organic phase is the starting material and product phase. It can optionally comprise further inert solvents which are immiscible or only slightly miscible with water. Examples of such inert solvents are toluene, benzene, xylenes, diethyl ether, methyl tert-butyl ether and alkanes such a hexane, pentane and octane.

The two phases are usually used in a volume ratio of the aqueous phase to the organic phase of from 10:1 to 1:10, in particular from 5:1 to 1:5.

A particular advantage in this connection is that the aqueous catalyst phase which has been separated off can be reused in the reaction. A prerequisite for this is the presence of two different liquid phases. If necessary, a small additional amount of fresh catalyst solution can be added in order to compensate for losses in activity.

The aqueous catalyst phase can also comprise from 1 to 50% by weight, in particular from 2 to 30% by weight, of additives which increase the catalytic activity. These may be substances which increase the lipophilicity of the aqueous phase, which brings about greater water solubility of the olefin used in the aqueous catalyst phase under the reaction conditions. Such substances are, for example, solubilizers or ammonium salts, alkali metal salts or alkaline earth metal salts.

The solubilizers which can be used for the reaction according to the invention are preferably chosen from the group consisting of mono-, di- and trialcohols (for example glycerol, methanol or ethanol), polyalkylene glycols, sulfolane (tetrahydrothiophene 1,1-dioxide), N-methylpyrrolidone, glyme (ethylene glycol dimethyl ether) and diglyme (diethylene glycol dimethyl ether).

Particularly suitable solubilizers are polyethylene glycols of the formula (I),

$$R^1-(OCH_2CH_2)_n-OR^2 \qquad (I)$$

in which $R^1$ is a hydrogen atom, a straight-chain or branched alkyl radical having from 1 to 4 carbon atoms or an hydroxyalkyl radical having from 1 to 4 carbon atoms, in particular a hydrogen atom, a methyl, hydroxymethyl or hydroxypropyl radical; $R^2$ is a methyl radical, in particular a hydrogen atom; and n is an integer between 2 and 20, in particular between 6 and 10.

Examples of such compounds are polyethylene glycols of the formula $H(OCH_2CH_2)_nOH$ having a mean molecular weight of approximately 200 (PEG 200), 400 (PEG 400), 600 (PEG 600) or 1000 (PEG 1000);

compounds of the formula $CH_3(OCH_2CH_2)_nOH$ having a mean molecular weight of approximately 350 (M 350), 500 (M 500) or 750 (M 750);

or compounds of the formula $CH_3CHOHCH_2(OCH_2CH_2)_nOH$ having a mean molecular weight of approximately 300 (300 PR), 450 (450 PR), 600 (600 PR) or 1000 (1000PR).

In the case of the polyethylene glycols of the formula $H(OCH_2CH_2)_nOH$, the designation PEG 200 means a mixture of polyethylene glycols of the formula $H(OCH_2CH_2)_nOH$ in which n is an integer from 3 to 6;

PEG 400 means a mixture of polyethylene glycols of the formula $H(OCH_2CH_2)_nOH$, in which n is an integer from 7 to 10;

PEG 600 means a mixture of polyethylene glycols of the formula $H(OCH_2CH_2)_nOH$, in which n is an integer from 11 to 16; and PEG 1000 means a mixture of polyethylene glycols of the formula $H(OCH_2CH_2)_nOH$, in which n is an integer from 15 to 30.

Each of these mixtures can be assigned a corresponding mean molecular weight of approximately 200 (PEG 200), about 400 (PEG 400), about 600 (PEG 600) and about 1000 (PEG 1000) respectively.

In the case of the compounds of the formula $CH_3(OCH_2CH_2)_nOH$ the designation M 350 means a mixture of compounds of the formula $CH_3(OCH_2CH_2)_nOH$ in which n is an integer from 5 to 9;

M 500 means a mixture of compounds of the formula $CH_3(OCH_2CH_2)_nOH$ in which n is an integer from 9 to 13: and M 750 means a mixture of compounds of the formula $CH_3(OCH_2CH_2)_nOH$ in which N is an integer from 12 to 20.

Each of these mixtures can be assigned a corresponding mean molecular weight of about 350 (M 350), about 500 (M 500) and 750 (M 750) respectively.

In the case of the compounds of the formula $CH_3CHOHCH_2(OCH_2CH_2)_nOH$, the designation 300 PR means a mixture of compounds of the formula $R(OCH_2CH_2)_nOH$ in which R is a β-hydroxypropyl radical $CH_3CHOHCH_2-$ and n is an integer from 6 to 9;

450 PR means a mixture of compounds of the formula $R(OCH_2CH_2)_nOH$ in which R is a β-hydroxypropyl radical $CH_3CHOHCH_2-$ and n is an integer from 8 to 14;

600 PR means a mixture of compounds of the formula $R(OCH_2CH_2)_nOH$ in which R is a β-hydroxypropyl radical $CH_3CHOHCH_2-$ and n is an integer from 12 to 20; and 1000 PR is a mixture of compounds of the formula $R(OCH_2CH_2)_nOH$, in which R is a β-hydroxypropyl radical $CH_3CHOHCH_2-$ and n is an integer from 18 to 26.

Each of these mixtures can be assigned a corresponding average molecular weight of about 300 (300 PR), about 450 (450 PR), about 600 (600 PR) and about 1000 (1000 PR) respectively.

Particularly good results are obtained using a polyethylene glycol which has a mean molecular weight of from 350 to 450, in particular of about 400.

Any desired mixtures of different polyethylene glycols, polyethylene glycol ethers (half ethers) and polyethylene glycol diethers can also be used.

The ammonium, alkali metal or alkaline earth metal salts are preferably from the group consisting of sodium iodide, potassium iodide, ammonium iodide, sodium chloride, potassium chloride, sodium bromide and potassium bromide. These salts increase the catalytic activity and the stability of the catalyst system.

In a preferred embodiment according to the invention, the catalyst additionally has at least one ligand which contains at least one phosphorus atom. This ligand is advantageously a water-soluble organic phosphine, in particular a sulfonated triaryl phosphine of the formula (II),

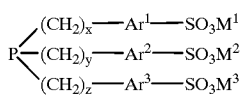

(II)

in which $Ar^1$, $Ar^2$ and $Ar^3$ independently of one another are each a phenyl, naphthyl, biphenyl, phenylnaphthyl or binaphthyl radical; x, y and z independently of one another are integers between 0 and 4, preferably between 1 and 2, in particular 1; and $M^1$, $M^2$ and $M^3$ independently of one another are each an alkali metal ion or an ammonium ion. It is, however, also possible at $M^1$, $M^2$ and $M^3$ or other higher-valency cations, such as, for example, alkaline earth metal or zinc cations, the charge balance decisively determining the number of these cations.

Trisulfonated triarylphosphines have proven particularly successful for the process according to the invention.

In this connection, particular preference is given to trisodium tri(m-sulfophenyl)phosphine, which conforms to the formula

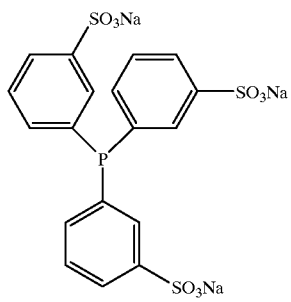

This trisodium salt, as a result of its preparation by sulfonation of triphenylphosphine, still also comprises amounts of mono- and disulfonated compounds and small amounts of the corresponding phosphine oxides.

The organic phosphine can also be a sulfonated triarylphosphine with two phosphorus atoms, which contain, for example, a radical —$(CH_2)_x$—Ar—Ar—$(CH_2)_x$—, in which x is an integer from 1 to 4, in particular from 1 to 2, preferably 1;

Ar—Ar is biphenyl or binaphthyl;

the —$(CH_2)_x$— group is bonded with one bond in each case in the ortho-position to the aryl-aryl bond Ar—Ar which joins the two aryl radicals, and with the other bond in each case to a phosphorus atom, each of which has two further, identical or different aryl radicals, in particular phenyl radicals.

Examples of such sulfonated triarylphosphines containing two phosphorus atoms are compounds of the formula (III)

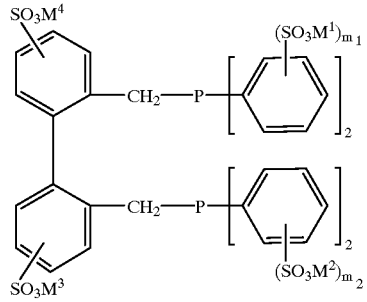

(III)

in which $m^1$ and $m^2$ may be 0 or 1, the sum of $m^1$ and $m^2$ being at least 1; and $M^1$, $M^2$, $M^3$ and $M^4$ independently of one another are each an alkali metal ion or an ammonium ion. Here, too, $M^1$, $M^2$ and $M^3$ may also be other higher-valency cations, such as, for example, alkaline earth metal or zinc cations, the charge balance again decisively determining the number of these cations.

The sulfonated triarylphosphine containing two phosphorus atoms can, however, also be a compound of the formula (IV)

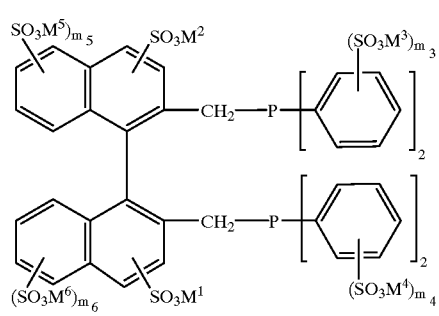

(IV)

in which $m_3$, $m_4$, $m_5$ and $m_6$ are 0 or 1, the sum of $m_3$, $m_4$, $m_5$ and $m_6$ being at least 2; and $M^1$, $M^2$, $M^3$, $M^4$, $M^5$ and $M^6$ independently of one another being as defined previously.

Such triarylphosphines containing two phosphorus atoms have at least three —$SO_3M$ radicals, in particular from four to eight —$SO_3M$ radicals, in which M has the same meaning as $M^1$ to $M^6$. The —$SO_3M$ radicals are usually on the aryl radicals of the radical —$(CH_2)_x$—Ar—Ar—$(CH_2)_x$— and on the two other aryl radicals which are bonded to the phosphorus.

Alternatively, instead of using sulfonated triarylphosphines ligands, it is possible to use other triarylphosphines in which the $SO_3M$ group is replaced by other groups which have an effect on the solubility of the triarylphosphine in water, such as, for example, $PO_3M_2$ groups.

The aqueous phase may contain from 5 to 2000 ppm of metals from group VIII of the Periodic Table of the Elements.

The aqueous phase containing the catalyst is preferably used in an amount corresponding to from $2 \times 10^{-6}$ to $5 \times 10^{-2}$ mol of the metals from group VIII of the Periodic Table of the Elements per mole of olefinic compounds.

The ratio of the metals of group VIII of the Periodic Table of the Elements to the ligand can be between 1:2 and 1:500, preferably between 1:5 and 1:200, in particular between 1:10 and 1:100.

The ratio of carbon monoxide and hydrogen can vary within wide limits. A favorable ratio of carbon monoxide to hydrogen is from 10:1 to 1:30, in particular from 5:1 to 1:8, particularly preferably from 1:2 to 1:5. It is likewise advantageous to inject synthesis gas in the ratio of carbon monoxide to water of 1:1 to 1:5, in particular from 1:1 to 1:3 and, if required, to inject pure hydrogen later over the course of the reaction.

Carbon monoxide and hydrogen can be added at a pressure of from 5 to 30 MPa, preferably from 10 to 18 MPa,.

The temperature during the reaction is normally between 60 and 200° C., preferably between 110 and 160° C., in particular between 135 and 150° C.

The reaction vessels used are preferably pressurized reactors fitted with a magnetic or mechanical stirring or mixing device. During the reaction, thorough mixing of the phases present, i.e. of the aqueous phase, carbon monoxide/hydrogen and, where present, of the organic phase, is to be ensured. This can be achieved in particular by intensive stirring and/or circulation of organic and aqueous phase.

The reaction is, for example, carried out by introducing initially the aqueous ammonia solution and the ligand with the rhodium and/or iridium compounds and any additives, and only then introducing carbon monoxide and hydrogen. This mixture can be preactivated for 0.5–3 hours at reaction temperature, and then the olefin and optionally the inert solvent(s) can be metered in using a pump. The reaction time is 1–50, preferably 3–20, hours. It is likewise possible to carry out the experiment continuously.

After the reaction has finished, the pressurized reactor is cooled and freed from carbon monoxide and hydrogen by decompression, and the reaction mixture is removed. When the mixing device is switched off, the phases separate of their own accord. The organic phase can be worked up by distillation and can then be examined by gas chromatography when required.

The examples below serve to illustrate the invention.

EXAMPLE 1

Comparative Example

In a 200 ml autoclave fitted with intensive magnetic stirrer is charged with 5.2 mg of rhodium acetate, 40 ml of 33% strength ammonia solution and 10 ml of a 0.5 molar aqueous solution of the sodium salt of triphenylphosphine-m-trisulfonic acid. 40 ml of ether and 17.4 g of 1-hexene are added as organic phase. 100 bar of hydrogen and 50 bar of carbon monoxide are injected, and a temperature of 140° C. is established. The consumed hydrogen and the consumed carbon monoxide are replenished by injecting fresh hydrogen and carbon monoxide.

After 6 hours, the autoclave is cooled and decompressed, and the organic phase is removed and examined using gas chromatography.

The conversion is 19.2% and the selectivity to primary heptylamines is 0%. The content of imines (isomeric imines formed from the condensation of intermediate aldehydes and primary amines) in the mixture is 7.6%, and that of secondary amines 0%.

EXAMPLE 2

A 200 ml autoclave fitted with an intensive magnetic stirrer is charged with 5.2 mg of rhodium acetate, 100 mg of chloro(1,5-cyclooctadiene)iridium(I) dimer, 40 ml of 33% strength ammonia solution and 10 ml of a 0.5 molar solution of the sodium salt of triphenylphosphine-m-trisulfonic acid. 30 ml of toluene and 5.8 g of 1-hexene are added as organic phase. 100 bar of hydrogen and 50 bar of carbon monoxide are injected, and a temperature of 140° C. is established. After 6 hours, the autoclave is cooled and decompressed, and the organic phase is removed and investigated by gas chromatography.

The conversion is 54%, and the selectivity to primary heptylamines is 60%. The amount of imines (isomeric imines formed from the condensation of intermediate aldehydes and primary amines) in the mixture is 12%, and that of secondary amines 1.7%.

EXAMPLES 3 TO 11

These examples are carried out as described in Example 2. The starting materials and their amounts and the reaction results are given in Table 1. In the case of Examples 3 to 8 and 10 to 12, two liquid phases were observed, but in the case of Example 9 only one phase.

In Table 1, the following designations are used:

Rh stands for rhodium acetate;

Ir stands for chloro(1,5-cyclooctadiene)iridium(I) dimer;

$H_2$ stands for hydrogen;

CO stands for carbon monoxide;

$NH_3$ stands for a 33% strength ammonia solution; in Example 12 only, $NH_3$ is ammonium acetate, and the amount is in grams;

TPPTS stands for trisodium tri(m-sulfophenyl)phosphine;

PEG 400 stands for a polyethylene glycol having a mean molecular weight of 400;

LM stands for the term solvent; ether stands for diethyl ether;

t designates the reaction time;

the selectivity based on the imines refers to isomeric imines which form from the condensation of intermediate aldehydes and primary amines;

THF stands for tetrahydrofuran.

EXAMPLE 12

A 200 ml autoclave fitted with intensive magnetic stirrer is charged with 5.2 mg of rhodium acetate, 100 mg of chloro(1,5-cyclooctadiene)iridium(I) dimer, 40 ml of demineralized water, 30 g of ammonium acetate and 10 ml of a 0.5 molar solution of the sodium salt of triphenylphosphine-m-trisulfonic acid. 40 ml of diethyl ether and 5.8 g of 1-hexene are added as organic phase. 125 bar of hydrogen and 25 bar of carbon monoxide are injected, and a temperature of 140° C. is established. After 360 minutes, the autoclave is cooled and decompressed, the aqueous phase is adjusted to a pH of 14 using NaOH, and the organic phase is removed and examined by gas chromatography. The conversion is 90.7% and the selectivity to primary heptylamines 56%. The amount of imines (isomeric imines formed from the condensation of intermediate aldehydes and primary amines) in the mixture is 0%, and that of secondary amines 9.4%.

EXAMPLE 13

A 200 ml autoclave fitted with intensive magnetic stirrer is charged with 26 mg of rhodium acetate, 100 mg of chloro(1,5-cyclooctadiene)iridium(I) dimer, 30 ml of 33% strength ammonia solution, 10 ml of demineralized water and 10 ml of a 0.5 molar solution of the sodium salt of triphenylphosphine-m-trisulfonic acid.

40 ml of diethylether and 8.5 g 1-propene are added as organic phase. 50 bar of synthesis gas ($CO/H_2$) and 50 bar of hydrogen are injected, and an internal temperature of 145° C. is established. Over the course of the experiment time of 360 minutes, synthesis gas/hydrogen is topped up. The $CO/H_2$ ratio should be 1:2. After the experiment has finished, the autoclave is cooled and decompressed, and the aqueous phase is separated from the organic phase.

A sample of the organic phase is taken and examined quantitatively by gas chromatography. The yield of the resulting amines was 61.2%, and the selectivity was 84.5% (see Table 2).

EXAMPLES 14 TO 22

Examples 14 to 22 were carried out in the same way as is described in Example 13. The amended conditions and the results are given in Table 2. The data "6.4 g $NH_3$" in Example 18 means that, in addition, 6.4 g of $NH_3$ are added as gas to the autoclave; this is achieved industrially by cooling the 30% strength ammonia solution, as a result of which the solubility for ammonia increases, and then adding ammonia gas to the cooled solution until the amount therein is 6.4 g.

EXAMPLE 23

A 200 ml autoclave fitted with intensive magnetic stirrer is charged with 2.3 mg of chloro(1,5-cyclooctadiene) rhodium(I) dimer, 50 mg of chloro(1,5-cyclooctadiene) iridium(I) dimer, 20 ml of 30% strength ammonia solution and 9 g of a BINAS solution (139 mmol of P(III) per kg). 18 ml of MTBE, 2.5 ml of isooctane (internal GC standard) and 2.5 g of 1-pentene are added as organic phase. 13 bar of carbon monoxide and 65 bar of hydrogen are injected, and then a temperature of 130° C. is established.

After 12 hours, the autoclave is cooled and decompressed, the organic phase is removed and the aqueous phase is subsequently extracted with 2×10 ml of MTBE. The combined organic phases are examined by gas chromatography.

The conversion is 42%, the selectivity as regards the secondary amine (di-(n-hexyl)amine) is 16.2%, 59.7% is the primary amine, and the ratio of linear to branched products is 99:1.

EXAMPLES 24 TO 26

These examples are carried out as described in Example 23. The starting materials and their amounts and also the reaction results are given in Table 3. In each of Examples 25 and 26, 19 ml of water are added to top up the aqueous phase. Prior to extraction of the aqueous phase after the reaction, in each of Examples 25 and 26, 10 ml of a 33% strength ammonia solution are added.

In Table 3, the following designations are used:

Rh stands for chloro(1,5-cyclooctadiene)rhodium(I) dimer;

Ir stands for chloro(1,5-cyclooctadiene)iridium(I) dimer $H_2$ stands for hydrogen CO stands for carbon monoxide $NH_3$ stands for a 33% strength ammonia solution BINAS stands for an aqueous solution of the octasodium salt of the octa-sulfonated ligand 1,1'-bisnaphthalene-2,2'-diylbis(methylene)-bis(diphenylphosphine) (NAPHOS);

LM stands for the term solvent, ether stands for diethyl ether, MTBE stands for methyl tert-butyl ether;

t stands for the reaction time;

n/i means the ratio of linear to branched product in the primary amines.

EXAMPLES 27 TO 30

These examples are carried out as described in Example 23. The starting materials and their amounts and also the reaction results are given in Table 4. In each of Examples 27 to 30, 19 ml of water are added to top up the aqueous phase. Prior to extraction of the aqueous phase after the reaction, in each of these examples, 10 ml of a 33% strength ammonia solution are added. Example 30 is a comparative example without the use of iridium.

In Table 2, the same designations as in Table 1 are used.

In Table 4, the same designations are used as in Table 1 or 2.

TABLE 1

| Ex. | Rh (in mg) | Ir (in mg) | $NH_3$ (in ml) | $H_2$ (in bar) | CO (in bar) | TPPTS (in ml) | PEG 400 (in g) | Olefin (in g) | LM (in ml) | t (in h) | Conversion | Selectivity, prim. amine (in %) | Selectivity sec. amines (in %) | Selectivity imines (in %) |
|---|---|---|---|---|---|---|---|---|---|---|---|---|---|---|
| 1 | 5.2 | — | 40 | 100 | 50 | 10 | — | 17.4 (1-hexene) | 40 (ether) | 6 | 19.2 | 0 | 0 | 7.6 |
| 2 | 5,.2 | 100 | 40 | 100 | 50 | 10 | — | 17.4 (1-hexene) | 40 (ether) | 6 | 73 | 62.0 | 3.7 | 15.2 |
| 3 | 5.2 | 100 | 40 | 100 | 50 | 10 | — | 5.8 (1-hexene) | 30 (toluene) | 3 | 54.0 | 60.0 | 1.7 | 12.0 |
| 4 | 5.2 | 100 | 40 | 125 | 25 | 10 | — | 5.8 (1-hexene) | 40 (ether) | 20 | 50 | 93.0 | 1.1 | 1.2 |
| 5 | 2.6 | 100 | 40 | 125 | 25 | 10 | — | 5.8 (1-hexene) | 40 (ether) | 20 | 42 | 90.0 | 0.7 | 2.0 |
| 6 | 10.4 | 100 | 40 | 125 | 25 | 10 | 10.0 | 5.8 (1-hexene) | 40 (ether) | 6 | 88 | 83.0 | 4.0 | 4.2 |
| 7 | 2.6 | 100 | 40 | 75 | 75 | 10 | 10.0 | 5.8 (1-hexene) | 30 (toluene) | 3 | 77 | 7.6 | 3.3 | 37.0 |
| 8 | 2.6 | 100 | 40 | 100 | 50 | 10 | 10.0 | 5.8 (1-hexene) | 30 (toluene) | 3 | 59 | 58.0 | 1.7 | 14.0 |
| 9 | 5.2 | 100 | 40 | 125 | 25 | 10 | — | 14.5 (1-pentene) | 30 (toluene) | 6 | 85 | 49.0 | 11.4 | 19.5 |
| 10 | 5.2 | 100 | 40 | 100 | 50 | 10 | — | 6.0 (norbornene) | 30 (toluene) | 6 | 100 | 65.0 | 10.0 | 25.0 |

TABLE 1-continued

| Ex. | Rh (in mg) | Ir (in mg) | NH₃ (in ml) | H₂ (in bar) | CO (in bar) | TPPTS (in ml) | PEG 400 (in g) | Olefin (in g) | LM (in ml) | t (in h) | Conversion | Selectivity, prim. amine (in %) | Selectivity sec. amines (in %) | Selectivity imines (in %) |
|---|---|---|---|---|---|---|---|---|---|---|---|---|---|---|
| 11 | 3.6 | 100 | 40 | 100 | 50 | 10 | — | 4.6 (cyclopentene) | 30 (toluene) | 6 | 47 | 74.0 | 5.0 | 5.0 |
| 12 | 5.2 | 100 | 30.0 (g) | 125 | 25 | 10 | — | 5.8 (1-hexene) | 40 (ether) | 6 | 90.7 | 56.0 | 9.4 | 0 |

TABLE 2

| Ex. | Rh (in mMol) | Ir (in mMol) | NH₃ (in ml) | H₂ (in bar) | CO (in bar) | TPPTS (in ml) | General exp. conditions | Olefin (in g) | Org. phase (in ml) | t (in h) | Yield % | Selectivity % |
|---|---|---|---|---|---|---|---|---|---|---|---|---|
| 13 | 0.1 | 0.3 | 30 | 75 | 25 | 10 | 140 bar 145° C. | 8.5 g (1-propene) | 40 (ether) | 6 | 61.2 | 84.5 |
| 14 | 0.02 | 0.1 | 20 | 75 | 25 | 10 | 179 bar 145° C. | 9.0 g (1-propene) | 40 (ether) | 6 | 61.1 | 60.6 |
| 15 | 0.02 | 0.1 | 20 | 52.5 | 17.5 | 10 | 105 bar 145° C. | 8.5 g (1-propene) | 40 (ether) | 6 | 41.9 | 56.3 |
| 16 | 0.05 | 0.1 | 30 | 100 | 50 | 20 | 210 bar 150° C. | 10.0 g (1-propene) | 40 (MTBE) | 6 | 42.1 | 57.7 |
| 17 | 0.02 | 0.1 | 40 | 90 | 30 | 5 | 168 bar 145° C. | 10 g (1-propene) | 40 (MTBE) | 6 | 40.7 | 76.7 |
| 18 | 0.02 | 0.3 | 30 6.4 g NH₃ | 125 | 25 | 20 | 240 bar 145° C. | 11.2 g (1-propene) | 20 (MTBE) | 6 | 47.5 | 76.4 |
| 19 | 0.1 | 0.3 | 30 | 100 | 50 | 20 | 285 bar 145° C. | 11.6 g (1-propene) | 40 (MTBE) | 6 | 44.7 | 79.4 |
| 20 | 0.005 | 0.3 | 40 | 114 | 36 | 20 | 191 bar 150° C. | 14.4 g (1-propene) | 30 (MTBE) | 6 | 33.1 | 50.6 |
| 21 | 0.02 | 0.3 | 40 | 125 | 25 | 10 | 158 bar 145° C. | 9.8 g (1-propene) | 40 (MTBE) | 6 | 47.3 | 98.1 |
| 22 | 5.2 | 0.3 | 40 | 125 | 25 | 10 | 162 bar 145° C. | 5.2 g (1-propene) | 30 (MTBE) | 6 | 28.3 | >99.0 |

TABLE 3

| Ex. | Rh (in mg) | Ir (in mg) | NH₃ (in ml) | H₂ (in bar) | CO (in bar) | BINAS (in g) | Olefin (in g) | LM (in ml) | Water (in ml) | t (in h) | Conversion (in %) | n/i prim. amine | Selectivity, prim. amine (in %) | Selectivity, sec. amine (in %) |
|---|---|---|---|---|---|---|---|---|---|---|---|---|---|---|
| 23 | 2.3 | 50 | 20 | 65 | 13 | 9.0 | 2.5 (1-pentene) | 18 (ether) | 0 | 8 | 42 | 99:1 | 59.7 | 16.2 |
| 24 | 4.6 | 25 | 20 | 65 | 13 | 9.0 | 2.5 (1-pentene) | 18 (MTBE) | 0 | 12 | 98 | 97:3 | 44.2 | 19.7 |
| 25 | 4.6 | 25 | 1.1 | 65 | 13 | 9.0 | 2.5 (1-pentene) | 18 (MTBE) | 19 | 12 | 99 | 99:1 | 2.8 | 85.0 |
| 26 | 2.3 | 12.5 | 1.1 | 65 | 13 | 4.5 | 2.5 (1-pentene) | 18 (MTBE) | 19 | 12 | 99 | 99:1 | 14.8 | 78.0 |

TABLE 4

| Ex. | Rh (in mg) | Ir (in mg) | NH₃ (in ml) | H₂ (in bar) | CO (in bar) | TPPTS (in g) | Olefin (in g) | LM (in ml) | t (in h) | Conversion (in %) | n/i prim. amine | Selectivity, prim. amine (in %) | Selectivity, sec. amine (in %) |
|---|---|---|---|---|---|---|---|---|---|---|---|---|---|
| 27 | 2.3 | 12.5 | 1.1 | 65 | 13 | 1.2 | 2.5 (1-pentene) | 18 (MTBE) | 12 | 80 | 78:22 | 37.6 | 61.2 |
| 28 | 2.3 | 12.5 | 1.1 | 65 | 13 | 4.8 | 2.5 (1-pentene) | 18 (MTBE) | 12 | 99 | 82:18 | 6.9 | 63.1 |

TABLE 4-continued

| Ex. | Rh (in mg) | Ir (in mg) | NH$_3$ (in ml) | H$_2$ (in bar) | CO (in bar) | TPPTS (in g) | Olefin (in g) | LM (in ml) | t (in h) | Conversion (in %) | n/i prim. amine | Selectivity, prim. amine (in %) | Selectivity, sec. amine (in %) |
|---|---|---|---|---|---|---|---|---|---|---|---|---|---|
| 29 | 7.1 | 38.4 | 3.2 | 65 | 13 | 3.7 | 7.0 (1-butene) | 18 (MTBE) | 12 | 98 | 92:8 | 0.8 | 90.5 |
| 30 | 2.3 | — | 1.1 | 65 | 13 | 2.4 | 2.5 (1-pentene) | 18 (MTBE) | 12 | 75 | n.b. | 0.2 | 6.2 |

We claim:

1. A process for the preparation of an amine in a single-stage reaction which comprises reacting a $C_2$–$C_{20}$-olefin with a compound having an NH$_3$ group, hydrogen, carbon monoxide and a catalyst, wherein
   a) the catalyst is dissolved or suspended in an aqueous phase comprising water, while the olefin is present in the non-aqueous phase, and
   b) the catalyst contains at least two metals from group VIII of the Periodic Table of Elements in elemental or bonded form.

2. A process as claimed in claim 1, wherein the amine is a primary or secondary amine.

3. A process as claimed in claim 1 or 2, wherein at least one of the metals from group VIII of the Periodic Table of the Elements is rhodium or iridium.

4. A process as claimed in claim 3, wherein the molar ratio of rhodium to iridium being between 2:1 and 1:200.

5. A process as claimed in claim 4, wherein the molar ratio of rhodium to iridium is between 1:1 and 1:100.

6. A process as claimed in claim 1 or 2, wherein the compound having an NH$_3$ group is ammonia or an ammonium compound.

7. A process as claimed in claim 6, wherein ammonia is used as gas or as gas dissolved in water, in a concentration of from 0.1 to 80% by weight, based on the aqueous phase.

8. A process as claimed in claim 7, wherein ammonia is used as gas or as gas dissolved in water in a concentration of from 5 to 80% by weight, based on the aqueous phase.

9. A process as claimed in claim 6, wherein the ammonium compound is used as aqueous solvent, in a concentration of from 1 to 80% by weight, based on the aqueous phase.

10. A process as claimed in claim 3, wherein the ammonium compound is used as aqueous solvent in a concentration of from 10 to 80% by weight, based on the aqueous phase.

11. A process as claimed in claim 10, wherein the ammonium compound is used as aqueous solvent in a concentration of from 20 to 40% by weight, based on the aqueous phase.

12. A process as claimed in claim 1 or 2, wherein, per mole of olefin, from 0.1 to 100 mol of the compound having an NH$_3$ group is used.

13. A process as claimed in claim 12, wherein, per mole of olefin, from 3 to 100 mol of the compound having an NH$_3$ group is used.

14. A process as claimed in claim 12, wherein, per mole of olefin, from 0.3 to 0.8 mol (for secondary amines) and from 5 to 20 mol (for primary amines) of the compound having an NH$_3$ group is used.

15. A process as claimed in claim 1 or 2, wherein the olefin under the reaction conditions is present in a liquid water-immiscible phase.

16. A process as claimed in claim 1 or 2, wherein the olefin has from 3 to 12 carbon atoms.

17. A process as claimed in claim 16, wherein the olefin is an olefin having up to 3 non-conjugated double bonds, a cycloolefin having up to 3 carbocycles, and an arylvinyl compound or mixture thereof.

18. A process a claimed in claim 16, wherein the olefin has one terminal or two non-conjugated double bonds.

19. A process as claimed in claim 18, wherein the olefin is chosen from the group consisting of propene, butene, isobutene, heptene, hexene and dicyclopentadiene.

20. A process as claimed in claim 1 or 2, wherein the aqueous phase further comprises at least one solubilizer.

21. A process as claimed in claim 20, wherein the solubilizer is selected from the group consisting of mono-, di- and trialcohols, polyalkylene glycole, sulfolane, N-methylpyrrolidone, glyme and diglyme.

22. A process as claimed in claim 20, wherein the solubilizer is a polyethylene glycol of the formula (I)

$$R^1-(OCH_2CH_2)_n-OR^2 \qquad (I)$$

in which
   $R^1$ is a hydrogen atom, a straight-chain or branched alkyl radical having from 1 to 4 carbon atoms or an hydroxyalkyl radical having from 1 to 4 carbon atoms,
   $R^2$ is a methyl radical or a hydrogen atom;
   n is an integer between 2 and 20.

23. A process as claimed in claim 22, wherein $R^1$ is a hydrogen atom, a methyl, hydroxymethyl or hydroxypropyl radical, $R^2$ is a hydrogen atom and n is an integer between 6 and 10.

24. A process as claimed in claim 22, wherein the polyethylene glycol has a mean molecular weight of from 350 to 450.

25. A process as claimed in claim 24, wherein the polyethylene glycol has a mean molecular weight of from 350 to about 400.

26. A process as claimed in claim 1 or 2, wherein the reaction is carried out in the presence of an additional ammonium, alkali metal or alkaline earth metal salt.

27. A process as claimed in claim 26, wherein the ammonium, alkali metal or alkaline earth metal salt is selected from the group consisting of sodium iodide, potassium iodide, ammonium iodide, sodium chloride, potassium chloride, sodium bromide and potassium bromide.

28. A process as claimed in claim 1 or 2, wherein the catalyst additionally contains at least one ligand which has at least one phosphorus atom.

29. A process as claim in claim 28, wherein the ligand is a water-soluble organic phosphine.

30. A process as claimed in claim 29, wherein the water-soluble organic phosphine is a sulfonated triarylphosphine of the formula (II)

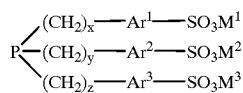
(II)

in which

Ar$^1$, Ar$^2$ and Ar$^3$ independently of one another are each a phenyl, naphthyl, biphenyl, phenylnaphthyl or binaphthyl radical;

x, y and z independently of one another are integers between 0 and 4; and

M$^1$, M$^2$ and M$^3$ independently of one another are each an alkali metal ion or an ammonium ion.

31. A process as claimed in claim 30, wherein x, y and z independently of one another are integers between 1 and 2.

32. The process as claimed in claim 31, wherein x, y and z are 1.

33. A process as claimed in claim 30, wherein the sulfonated triarylphosphine is trisulfonated triarylphosphine.

34. A process as claimed in claim 33, wherein the trisulfonated triarylphosphine is trisodiumtri-(m-sulfophenyl)phosphine.

35. A process as claimed in claim 29, wherein the organic phosphine is a compound of the formula (III)

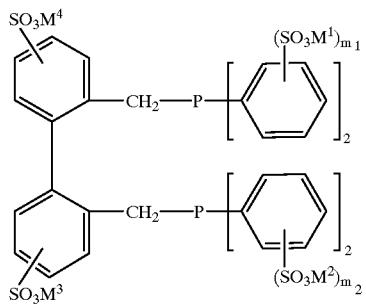
(III)

in which m$^1$ and m$^2$ may be 0 or 1, the sum of m$^1$ and m$^2$ being at least 1; and M$^1$, M$^2$, M$^3$ and M$^4$ independently of one another are each an alkali metal ion or an ammonium ion.

36. A process as claimed in claim 29, wherein the organic phosphine is a compound of the formula (IV)

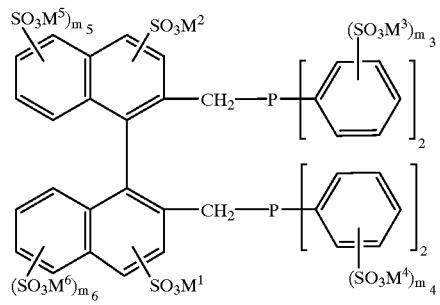
(IV)

in which m$_3$, m$_4$, m$_5$ and m$_6$ may be 0 or 1, the sum of m$_3$, m$_4$, m$_5$ and m$_6$ being at least 2; and M$^1$, M$^2$, M$^3$, M$^4$, M$^5$ and M$^6$ independently of one another are each an alkali metal ion or an ammonium ion.

37. A process as claimed in claim 1 or 2, wherein the aqueous phase contains from 5 to 2000 ppm of metals from group VIII of the Periodic Table of the Elements.

38. A process as claimed in claim 1 or 2, wherein the aqueous phase containing the catalyst is used in an amount corresponding to from $2 \times 10^{-6}$ to $5 \times 10^{-2}$ mol of the metals from group VIII of the Periodic Table of the Elements per mole of olefinic compound.

39. A process as claimed in claim 1 or 2, wherein the ratio of the metals of group VIII of the Periodic Table of the Elements to the ligand is between 1:2 and 1:500.

40. A process as claimed in claim 39, wherein the ratio of the metals of group VIII of the Periodic Table of the Elements to the ligand is between 1:5 and 1:200.

41. A process as claimed in claim 40, wherein the ratio of the metals of group VIII of the Periodic Table of the Elements to the ligand is between 1:10 and 1:100.

42. A process as claimed in claim 1 or 2, wherein carbon monoxide and hydrogen are added at a pressure of from 5 to 30 Mpa, where the ratio of carbon monoxide to hydrogen is between 10:1 and 1:30.

43. A process as claimed in claim 42, wherein carbon monoxide and hydrogen are added at a pressure of from 10 to 18 MPa.

44. A process as claimed in claim 1 or 2, wherein the temperature during the reaction is between 60 and 200° C.

45. A process as claimed in claim 44, wherein the temperature during the reaction is between 110 and 160° C.

46. A process as claimed in claim 45, wherein the temperature during the reaction is between 135 and 150° C.

* * * * *